(12) United States Patent
Calvert

(10) Patent No.: US 9,669,237 B2
(45) Date of Patent: Jun. 6, 2017

(54) COMBINED MRI AND RADIATION THERAPY EQUIPMENT

(75) Inventor: Simon James Calvert, Oxfordshire (GB)

(73) Assignee: Siemens PLC, Camberley (GB)

( * ) Notice: Subject to any disclaimer, the term of this patent is extended or adjusted under 35 U.S.C. 154(b) by 728 days.

(21) Appl. No.: 14/112,741

(22) PCT Filed: Mar. 8, 2012

(86) PCT No.: PCT/EP2012/053981
§ 371 (c)(1),
(2), (4) Date: Oct. 25, 2013

(87) PCT Pub. No.: WO2012/143173
PCT Pub. Date: Oct. 26, 2012

(65) Prior Publication Data
US 2014/0107468 A1   Apr. 17, 2014

(30) Foreign Application Priority Data
Apr. 21, 2011  (GB) .................................. 1106822.8

(51) Int. Cl.
*A61B 5/055* (2006.01)
*A61N 5/10* (2006.01)
(Continued)

(52) U.S. Cl.
CPC ............ *A61N 5/1039* (2013.01); *A61B 5/055* (2013.01); *A61N 5/1077* (2013.01);
(Continued)

(58) Field of Classification Search
CPC ............ A61B 5/055; A61N 2005/1055; A61N 5/1039; A61N 5/1077; A61N 5/1081;
(Continued)

(56) References Cited

U.S. PATENT DOCUMENTS

2005/0104701 A1* 5/2005 Huang ............... G01R 33/3815
335/300
2006/0193435 A1  8/2006 Hara et al.
(Continued)

FOREIGN PATENT DOCUMENTS

| WO | 2009156896 | 12/2009 |
| WO | 2011042820 | 4/2011 |
| WO | 2011063342 | 5/2011 |

OTHER PUBLICATIONS

Raaymakers et al., "Integrating a 1.5 T MRI Scanner With a 6 MV Accelerator: Proof of Concept", Phys. Med. Biol. 54 (2009) N229-N237. Published May 19, 2009.
(Continued)

*Primary Examiner* — Ruth S Smith
(74) *Attorney, Agent, or Firm* — Schiff Hardin LLP

(57) ABSTRACT

In a combined MRI and radiation therapy system, a magnet structure and radiation therapy equipment are provided. The magnet structure comprises a single substantially cylindrical field coil structure comprising a number of superconducting coils joined by a support structure and extending axially of a central region. An outer vacuum chamber encloses the field coil structure in an evacuated volume. A cooling arrangement comprising cooling tubes is in thermal contact with the superconducting coils and receives a cryogen flowing through the cooling tubes. The radiation therapy equipment comprises a gamma radiation source rotatable about an axis of the field coil structure to direct a radiation beam substantially radially through the field coil structure. Parts of the field coil structure and the outer vacuum chamber are transparent to radiation emitted by the gamma radiation source whereby the radiation beam is directed through the field coil structure and the outer vacuum chamber without substantial interference.

11 Claims, 3 Drawing Sheets

(51) Int. Cl.
  *G01R 33/3815*   (2006.01)
  *G01R 33/48*     (2006.01)
  *G01R 33/38*     (2006.01)

(52) U.S. Cl.
  CPC ......... *A61N 5/1081* (2013.01); *A61N 5/1082* (2013.01); *G01R 33/3804* (2013.01); *G01R 33/3815* (2013.01); *G01R 33/4808* (2013.01); *A61N 2005/1055* (2013.01)

(58) Field of Classification Search
  CPC .............. A61N 5/1082; G01R 33/3804; G01R 33/3815; G01R 33/4808
  See application file for complete search history.

(56) References Cited

U.S. PATENT DOCUMENTS

| | | |
|---|---|---|
| 2009/0128270 A1 | 5/2009 | Calvert |
| 2011/0043207 A1 | 2/2011 | Gross |
| 2011/0074421 A1* | 3/2011 | Sakakura ........... G01R 33/3856 324/318 |

OTHER PUBLICATIONS

M. Lakrimi et al., "The Principles and Evolution of Magnetic Resonance Imaging", Journal of Physic: Conference Series 286 (2011), pp. 1-11.

* cited by examiner

COMBINED MRI AND RADIATION THERAPY EQUIPMENT

BACKGROUND

The present disclosure relates to a combined MRI and radiation therapy system. In particular, it relates to such a system which is compact, inexpensive and employs a background magnetic field for MRI imaging with high magnetic flux.

Recently, attempts have been made to combine imaging systems with therapy systems, particularly in the field of radiation therapy, as such combined systems allow localization of tumors as, or immediately before, the treatment beam is applied. This ensures that the treatment beam is correctly targeted, in turn meaning that treatment may be more effective and that unintentional irradiation of healthy tissue is minimized.

Certain radiation therapy systems utilize highly penetrating gamma-like radiation to kill cancerous tissue. Gamma radiation is generally regarded as electromagnetic radiation having a wavelength of between $10^{-10}$ m and $2\times10^{-13}$ m, or quantum energy in the range $10^4$ eV to $5\times10^6$ eV. High energy x-rays also fall within this range, and the present description should be understood in the sense that "gamma radiation" includes all electromagnetic radiation of sufficient energy to be useful in radiation therapy applications.

Gamma radiation is not perturbed by magnetic fields and can only be screened by the use of significant amounts of dense material such as lead or concrete. Radiation of this type is normally generated by either small linear accelerators or by gamma-emitting radioactive sources such as cobalt-60. Since linear accelerators are affected by background magnetic fields, the second of these options is preferred in the present preferred embodiment, as the magnetic field required by the MRI system will not interfere with the generation of gamma radiation using a radioactive source.

Previously, separate MRI and radiation therapy systems were used but this was found to be far from ideal. Problems with organ motion and image registration led to poor utilization of the available radiation dose and accidental necrosis of viable tissue.

More recently, some superconducting magnet configurations have been developed for combined MRI and radiation therapy applications, using split magnets with a rotating gamma source in the gap between the two parts of the magnet. The resulting complex, cumbersome designs have relatively low field and poor homogeneity due to the necessarily large axial distance between the center-most coils of the magnet. The need to accommodate a rotating Gamma source in the gap means that the problem of supporting the two cryostat halves with respect to each other presents many difficulties. Mechanical difficulties associated with restraining the forces generated between the two halves of the magnet lead to further cumbersome arrangements.

SUMMARY

The present preferred embodiments accordingly provide combined MRI and radiation therapy systems.

In a combined MRI and radiation therapy system, a magnet structure and radiation therapy equipment are provided. The magnet structure comprises a single substantially cylindrical field coil structure comprising a number of superconducting coils joined by a support structure and extending axially of a central region. An outer vacuum chamber encloses the field coil structure in an evacuated volume. A cooling arrangement comprising cooling tubes is in thermal contact with the superconducting coils and receives a cryogen flowing through the cooling tubes. The radiation therapy equipment comprises a gamma radiation source rotatable about an axis of the field coil structure to direct a radiation beam substantially radially through the field coil structure. Parts of the field coil structure and the outer vacuum chamber are transparent to radiation emitted by the gamma radiation source whereby the radiation beam is directed through the field coil structure and the outer vacuum chamber without substantial interference.

The above, and further, objects, characteristics and advantages of the present preferred embodiments will be more apparent from the following description of those certain embodiments thereof, in conjunction with the appended drawings.

DESCRIPTION OF EXEMPLARY EMBODIMENTS

Figure 1:
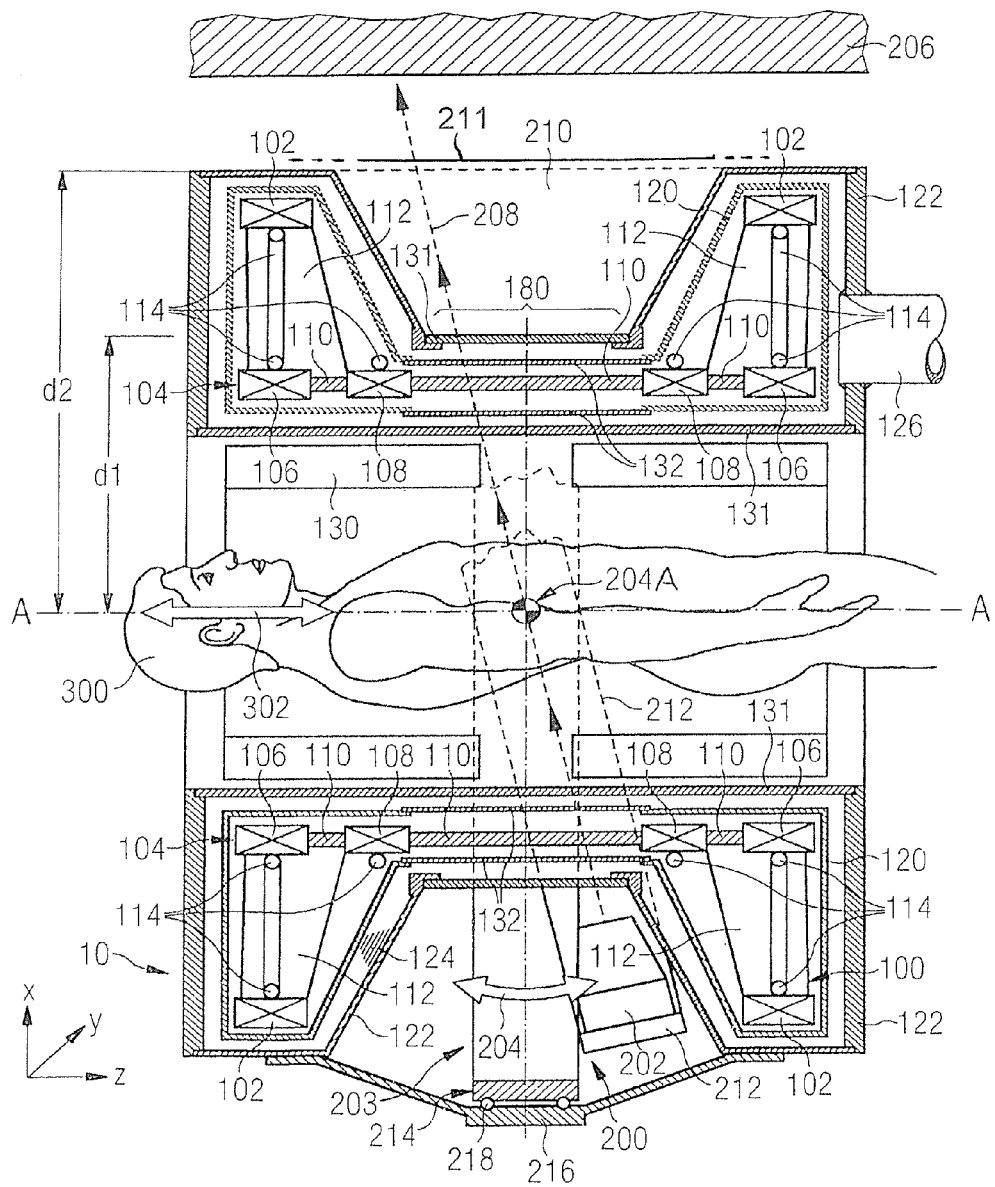
FIG. 1 shows an axial cross-section of a combined MRI and radiation therapy system of the present preferred embodiments invention.

For the purpose of promoting an understanding of the principles of the invention, reference will now be made to preferred exemplary embodiments/best mode illustrated in the drawings and specific language will be used to describe the same. It will nevertheless be understood that no limitation of the scope of the invention is thereby intended, and such alterations and further modifications in the illustrated embodiments and such further applications of the principles of the invention as illustrated as would normally occur to one skilled in the art to which the invention relates are included herein.

The present exemplary embodiments particularly relate to essentially cylindrical magnets. The term "axial" is used herein to denote direction parallel to the axis of a cylindrical magnet, while the term "radial" is used to indicate direction perpendicular to axial directions.

The present exemplary embodiments provide a closely integrated MRI and radiation therapy system without compromising the functionality or either and, in particular, without compromising the performance, appearance and cost of the superconducting magnet.

The present exemplary embodiments provide a magnet configuration which enables a combined MR and radiation therapy system to be realized without resort to a split magnet. This will allow a superconducting magnet of magnetic flux density 1.5 T or 3 T or more to be used thus enabling better spatial imaging resolution and/or faster imaging than is possible on existing systems, in which the mechanical forces between parts of a split magnet limit the magnetic flux density which can be used in such combined MRI and radiation therapy systems.

The cost of the proposed system is expected to be inherently lower than for the known split magnet designs, for example due to the simpler manufacturing method for more conventional coil geometry; and simpler, un-split, cryostat design.

FIG. 1 illustrates an axial cross-section through a combined MRI and radiation therapy system 10 of an exemplary embodiment of the present invention.

The MRI system includes a magnet structure 100 which includes shield coils 102 and field coils 104, the field coils including end coils 106 and inner coils 108. The field coils 104 are held in their relative positions by a field coil support structure 110. Shield coils 102 are of greater diameter than the field coils, and are held in their relative positions by field coil supports 112. Cooling tubes 114 are provided in thermal contact with the coils 102-108. The cooling tubes carry a cryogen and serve to cool the coils to below the superconducting transition temperature of the material of the coils. For example, the coils may be cooled to approximately 4K. Surrounding the magnet structure 100 is a thermal radiation shield 120 which is cooled by suitable means (not shown) to a temperature intermediate the temperature of the coils and the ambient temperature. Surrounding the thermal radiation shield 120 is an outer vacuum container (OVC) 122, which is at ambient temperature. The volume within the OVC, including the volume between the thermal radiation shield and the magnet structure 100, is evacuated to a hard vacuum, as is conventional, to provide thermal insulation between the magnet structure 100, the thermal radiation shield 120 and the OVC 122. Solid insulation 124 may be provided in the volume between the OVC 122 and the thermal radiation shield 120. The presence of thermal radiation shield 120 and solid insulation 124 is not a requirement of the present exemplary embodiment, and they may be omitted provided that sufficient cooling is provided to cool the coils 104, 102 to below their superconducting transition temperature.

Connection 126 is a passageway allowing the cooling pipes 114 to pass out of the OVC to connect to a remote reservoir of cryogen fluid. Such arrangement will be discussed in more detail below. The inner volume of connection 126 is evacuated, typically being exposed to the evacuated inner volume of the OVC. The MRI system also comprises a gradient coil assembly 130 which, as is well known, contains electromagnet coils which generate oscillating magnetic field gradients in mutually perpendicular directions. The MRI system will also comprise conventional control systems, power supplies, RF coils for generating and receiving high frequency magnetic fields to generate MRI images, and other equipment, as is conventional in itself, but such components do not directly relate to the present exemplary embodiment, and so are not illustrated or described in detail herein.

The radiation therapy equipment 200 includes a gamma source 202, for example containing cobalt-60 mounted on a gimbal arrangement 203 which allows the source 202 to rotate about axis A-A and to pivot, as indicated by double arrow 204 about a gimbal pivot indicated at 204A. This equipment is essentially at ambient temperature.

A suitable radiation shielding 206 may be provided, sufficient to receive gamma radiation 208 emitted from the gamma source 202 in any of its possible locations. In the illustrated arrangement, the gamma source 202 may be constrained to rotate only in a lower semicircular arc, with radiation shielding 206 provided in a corresponding upper semicircular arc. Radiation shielding may be a layer of lead or concrete of sufficient thickness to absorb a beam of gamma radiation 208 emitted by the gamma source 202.

Patient 300 is schematically illustrated in FIG. 1, and will be positioned on a patient bed (not shown), enabling the patient to be moved 302 in an axial direction relative to the magnet structure and the radiation therapy equipment on the patient bed. Conventional patient beds are known, constructed of materials which are transparent to gamma radiation. Such gamma-transparent materials include materials of low atomic number such as beryllium, carbon and aluminum. Resin-impregnated carbon fibre may be used. Such a gamma-transparent patient bed should be used in systems of the present exemplary embodiment.

In the illustrated embodiment, the arrangement of coils 102, 104 is such that the OVC may be "waisted"—that is, an axially central portion of the OVC has a lesser outer diameter d1 than the outer diameter d2 of the axially outer portions of the OVC. This provides a toroidal cavity 210, and the gimbal arrangement 203 and the gamma source 202 are substantially accommodated within the toroidal cavity 210. The exemplary embodiment does not, however, require such a waisted OVC, and may be embodied by a cylindrical OVC with the gimbal arrangement and gamma source being arranged radially further from axis A-A than the outer surface of the OVC 122.

Gimbal arrangement 203 comprises a pivoting gimbal ring 212 which retains the radiation source 202, and is able to rotate 204 by a limited amount about gimbal pivot 204, which joins the pivoting gimbal ring 212 to a rotating gimbal ring 214 arranged to rotate about axis A-A. An outer fixed gimbal ring 216 is in a fixed relative position compared to the OVC, and bearings 208, such as ball bearings or rollers, are provided between the outer fixed gimbal ring 218 and the rotating gimbal ring 214 to allow the latter to rotate within the former. Using the gimbal arrangement, it is possible to arrange the gamma beam 208 to reach the patient 300 from any angle within the range of rotation of the gamma source, and at any angle within the range of rotation about the gimbal pivot 204. Such gimbal arrangements are known in themselves in combination with known split magnet MRI systems of the prior art.

The present exemplary embodiment proposes an optimal magnet configuration suitable for the realization of a combined MRI and radiation therapy system. In such a system, a patient 300 is typically imaged to locate a tumor to be treated. The tumor would then be targeted with radiation from radiation source 202 by suitably positioning the source 202 with respect to the patient. Two available dimensions: rotation about axis A-A in an X-Y plane, and inclination of the source 202 with respect to the XY plane by rotation of the pivoting gimbal ring 212 about the gimbal pivot 204 are provided by the gimbal arrangement 203. A third dimension of relative motion between the patient and the source 202 is provided by motion 302 of the patient in the Z direction by movement of the patient table. As is conventional, multiple irradiation steps may be performed on a tumor, from different angles, to ensure a high radiation dose in the tumour, with a tolerably low radiation dose in healthy tissue. Following irradiation of the tumor, the patient would be re-imaged by the MRI system of the apparatus to ensure that all of the tumor has been killed. Further irradiation steps may be performed if the MRI imaging reveals that not all of the tumor has been killed. MRI imaging is capable of clearly distinguishing between live and dead tissue.

As the gamma radiation source and the gamma radiation itself are not affected by the presence of a magnetic field, the radiation therapy may be performed while the background magnetic field of the MRI system, generated by coils 102-108, is present. It may be found possible to perform imaging as the radiation therapy is performed, with the gradient coil assembly 130 generating oscillating magnetic fields at the same time.

The combined MRI and radiation therapy system of the exemplary embodiment allows accurate targeting of tumors in very mobile organs such as the lungs. The beam targeting and collimation (conventional in themselves, and not described in detail here) can be adjusted, almost in real time, to compensate for organ movement during therapy. This allows effective use of the allowable patient dose by avoiding re-dosing parts of the tumor which are already dead. The ability of the present exemplary embodiment to employ a magnet structure 100 generating high magnetic flux density enables improved imaging over conventional combined MRI and radiation therapy systems using a split magnet, which has a background field of much lower magnetic flux density.

In order to allow a single essentially cylindrical magnet structure 100 which permits application of radiation therapy of a patient while in position within the magnet, it must be possible to apply the radiation beam 208 through the structure of the magnet 100 including the OVC 122, and the thermal radiation shield 120.

This is achieved, according to a feature of the present exemplary embodiment, by elimination of virtually all dense structures from those parts of the magnet, OVC and thermal radiation shield which lie within a path of the radiation beam 208 which may be selected for use in a radiation therapy irradiation step. Those parts may be conveniently referred to as a "central region" 180.

Conventionally, MRI magnets have been constructed by winding coils of superconducting wire onto an aluminum former. The magnet of the present exemplary embodiment does not employ an aluminum former, but uses an alternative assembly process to ensure that the magnet structure does not impede the passage of the radiation beam 208. In the illustrated embodiment, and as will be discussed in further detail with reference to FIG. 2, this is achieved by assembling the magnet structure 100 from alternating cylindrical annular components, being impregnated coils 106, 104 and support tubes 110. The support tubes can be complete cylinders, or may have cut-outs extending partially or intermittently around the circumference. Other coil support structures may be employed, for example a mounting cylinder having coils mounted by their radially outer surfaces onto the radially inner surface of the cylinder.

The central support tube 110, through which the radiation beam 208 must be able to pass, may include a region which is transparent to the gamma radiation of radiation beam 208. This may be achieved by forming the central support tube from a suitable gamma-transparent material, or including a "window" of suitable material within the appropriate part of the central support tube. Suitable gamma-transparent materials for forming such windows or transparent support tubes include materials with very low atomic number, such as beryllium and graphite/carbon composites.

A similar structure may be applied to a corresponding part of a mounting cylinder, where used.

Cooling of the superconducting magnet coils 102-108 is achieved by passing cryogen coolant through cooling pipes 114 in thermal contact with superconducting coils 102, 106, 108. The cooling pipes are joined by a manifold (not visible in FIG. 1) comprised of suitable gamma-transparent materials such as those described above, at least where such manifold lies within a path of the radiation beam 208 which may be selected for use in a radiation therapy irradiation step. The cooling pipes 114 are provided with cryogen from a remote reservoir such as will be discussed with reference to FIGS. 2 and 3. The reservoir is preferably kept away from any path of the radiation beam 208 which may be selected for use in a radiation therapy irradiation step, and is preferably vacuum insulated by being located within a volume open to the evacuated interior of the OVC.

The OVC 112 includes gamma-transparent inner and outer tube sections 130 manufactured from materials such as graphite composites or CFRP. Such materials are already used to manufacture X-ray transparent patient beds for radiation therapy systems and CT scanners. In the illustrated embodiment, the outer gamma-transparent tube section 130 occupies only the central "waisted" portion of the outer cylindrical surface of the OVC, while the inner gamma-transparent tube section 130 occupies the entire inner cylindrical surface of the OVC. In alternative embodiments, the inner gamma-transparent tube section 130 may occupy only a central part of the inner cylindrical surface of the OVC, or the outer gamma-transparent tube section 130 may occupy the entire inner cylindrical surface of the OVC, as appropriate to the construction of the OVC. The gamma-transparent tube sections 130 should occupy at least all of those parts of the OVC which lie within a path of the radiation beam 208 which may be selected for use in a radiation therapy irradiation step.

Similarly, gamma-transparent sections 132 should be provided in the thermal radiation shield 120 at least for all of those parts of the thermal radiation shield 120 which lie within a path of the radiation beam 208 which may be selected for use in a radiation therapy irradiation step. Choice of material for the gamma-transparent sections 132 of the thermal radiation shield should favor materials which are also thermally conductive, and relatively opaque to infra-red radiation, to enable the thermal radiation shield to block infra-red radiation from reaching the cryogenically cooled superconducting magnet coils 102, 106, 108. Alternatively, while being less preferred, cut-outs may be provided in the thermal radiation shield, such that the thermal radiation shield is absent in any path of the radiation beam 208 which may be selected for use in a radiation therapy irradiation step.

Preferably, in a finished combined MRI and radiation therapy system according to the present exemplary embodiment, looks covers will be provided to enclose the entire system in an aesthetically attractive outer cover. The provision of a waisted section of the OVC and the location of the radiation source 202 within the annular cavity 210 provided by the waisted section means that the final appearance of the system will be similar to that of a conventional cylindrical-magnet MRI system. This may reduce anxiety in the patient, and will increase the chances of effective imaging and treatment as the patient may be more relaxed than if confronted with the appearance of conventional combined MRI and radiation therapy systems. A portion 211 of the cover that covers the waisted section is schematically shown in FIG. 1. This may reduce anxiety in the patient, and will increase the chances of effective imaging and treatment as the patient may be more relaxed than if confronted with the appearance of conventional combined MRI and radiation therapy systems.

Figure 2:
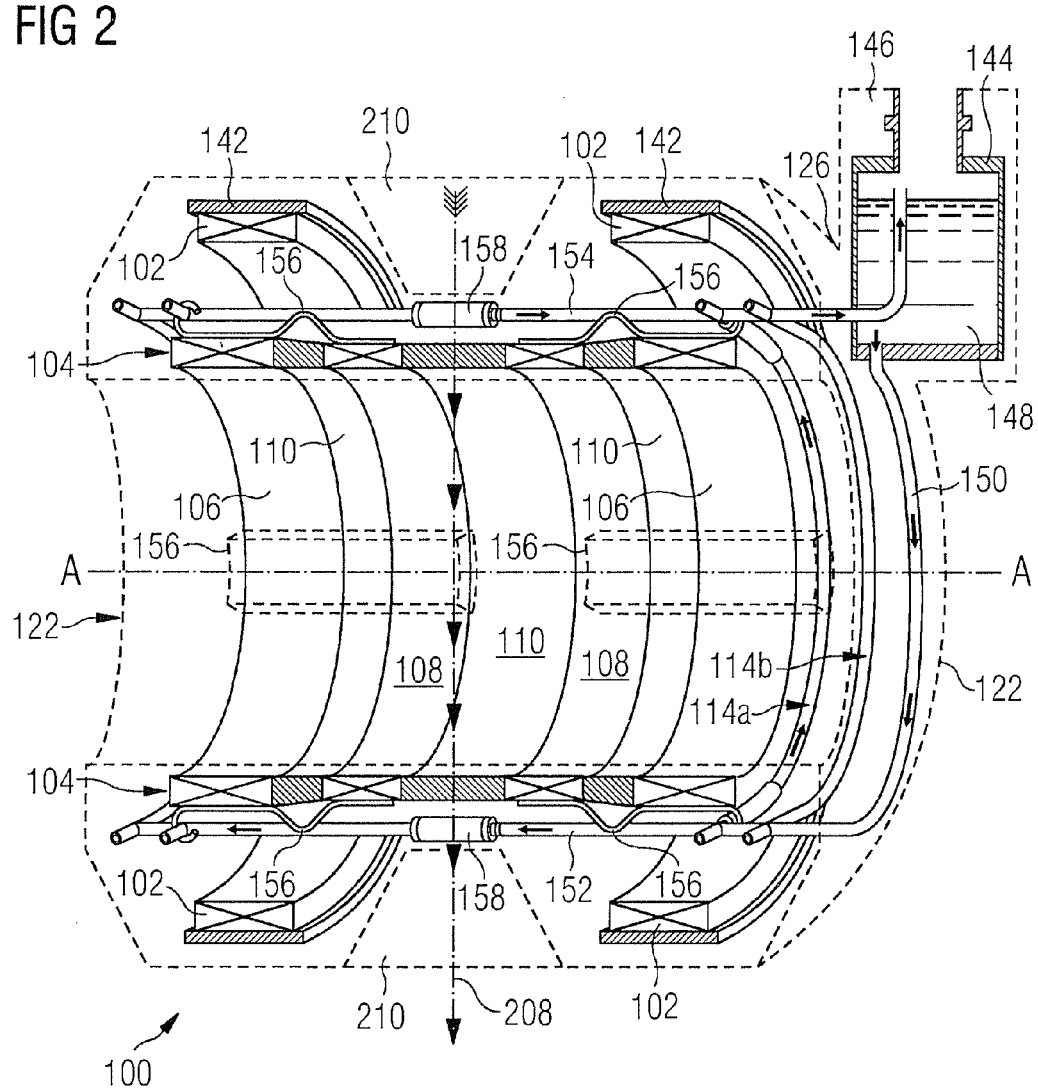
FIG. 2 shows a cut-away view of a coil arrangement with cooling and support structures, suitable for inclusion in a combined MRI and radiation therapy system of the present preferred embodiments.

FIG. 2 shows a cutaway view of a magnet structure 100 comprising a coil arrangement with cooling and support structures, suitable for inclusion in a combined MRI and radiation therapy system of the present exemplary embodiment such as illustrated in FIG. 1. Features corresponding to features illustrated in FIG. 1 carry corresponding reference numerals. An example beam of gamma radiation 208 is illustrated for reference, along with a representation of the OVC 122 in phantom.

In this example, shield coils 102 are mounted by their radially outer surfaces to a radially outer support 142 which may be composed of resin-impregnated glass fiber, for example. The radially outer supports are mounted within the OVC by appropriate means, not illustrated. The field coils 104 are bonded by their axial extremities to annular or cylindrical support structures 110. As discussed above, at least the central support structure is of gamma-transparent material, at least in those portions which lie within a path of the radiation beam 208 which may be selected for use in a radiation therapy irradiation step. This structure is supported by the support structures within the OVC 122 by appropriate means, not illustrated.

FIG. 2 particularly illustrates a cooling arrangement suitable for use in the present exemplary embodiment. The cooling arrangement is one commonly referred to as a "cooling loop". A remote cryogen reservoir 144 is provided, vacuum insulated from ambient temperature by inclusion within a vacuum region 146 exposed to the interior of the OVC 122. Cryogen reservoir 144 contains a cryogen 148 which is arranged to circulate through cooling pipes 114. In the illustrated example, liquid cryogen is gravity-fed through a feed pipe 150 to a lower manifold 152. The lower manifold 152 joins feed pipe 150 to a first cooling circuit 114*a*, which is in thermal contact with field coils 106, 108, and to a second cooling circuit 114*b*, which is in thermal contact with shield coils 102. Cryogen passes through first and second cooling circuits 114*a*, 114*b*, extracting heat from the coils. This will cause the cryogen to expand, and possibly boil. This reduction in density will cause the cryogen to rise within the cooling circuit to an upper manifold 154 which joins upper parts of first and second cooling circuits 114*a*, 114*b* to the cryogen reservoir 144. The gravity feed of cryogen into the feed pipe 150 will displace the cryogen through upper manifold 154 back into the cryogen reservoir 144. Preferably, an active cooling arrangement such as a cryogenic refrigerator is provided to re-cool the cryogen returned to the cryogen reservoir, in preparation for re-circulation through the first and second cooling circuits. Unlike the example of FIG. 1, cooling pipes 114 are not provided in thermal contact with each coil. Rather, thermally conductive straps 156 are provided, each in thermal contact with at least one cooling pipe 114 and at least one coil 106, 108. Coils are cooled by thermal conduction through cooling straps 156 to cooling pipe 114, which is cooled by circulation of cryogen as described above. The thermally conductive straps 156 may be solid straps of a conductive material such as aluminum or copper, or may be a braid or laminate of such materials, or any other suitable thermally conductive material. Similarly, the cooling pipes 114 may be of aluminum or copper or any other suitable thermally conductive material. The material of the cooling straps 156 and the cooling pipes is preferably non-magnetic. The cooling straps do not extend into the axially central region of the magnet structure which lies within a path of the radiation beam 208 which may be selected for use in a radiation therapy irradiation step.

Feed pipe 150 and upper and lower manifolds 152, 154 need not be of thermally conductive materials. As shown in FIG. 2, the upper and lower manifolds 152, 154 of the cooling arrangement extend across an axially central region of the magnet assembly, in the region where radiation beams 208 will be directed during radiation therapy treatment. To prevent these manifolds from interfering with the radiation therapy beam 208, those portions 158 of the manifolds which lie within a path of the radiation beam 208 which may be selected for use in a radiation therapy irradiation step are composed of a gamma-transparent material, such as those gamma-transparent materials described above. Ceramic materials may be preferred for the gamma-transparent parts of the manifolds.

Accordingly, all parts of the magnet structure, the OVC and the thermal radiation shield, if any, in the central region 180 within any path of the radiation beam 208 which may be selected for use in a radiation therapy irradiation step, are transparent to the gamma radiation emitted by the radiation source 202, such that a radiation beam 208 may be directed through the structure of the MRI magnet and its cryostat to act upon patient 300 without substantial interference from the structure of the MRI magnet and its cryostat.

Figure 3:
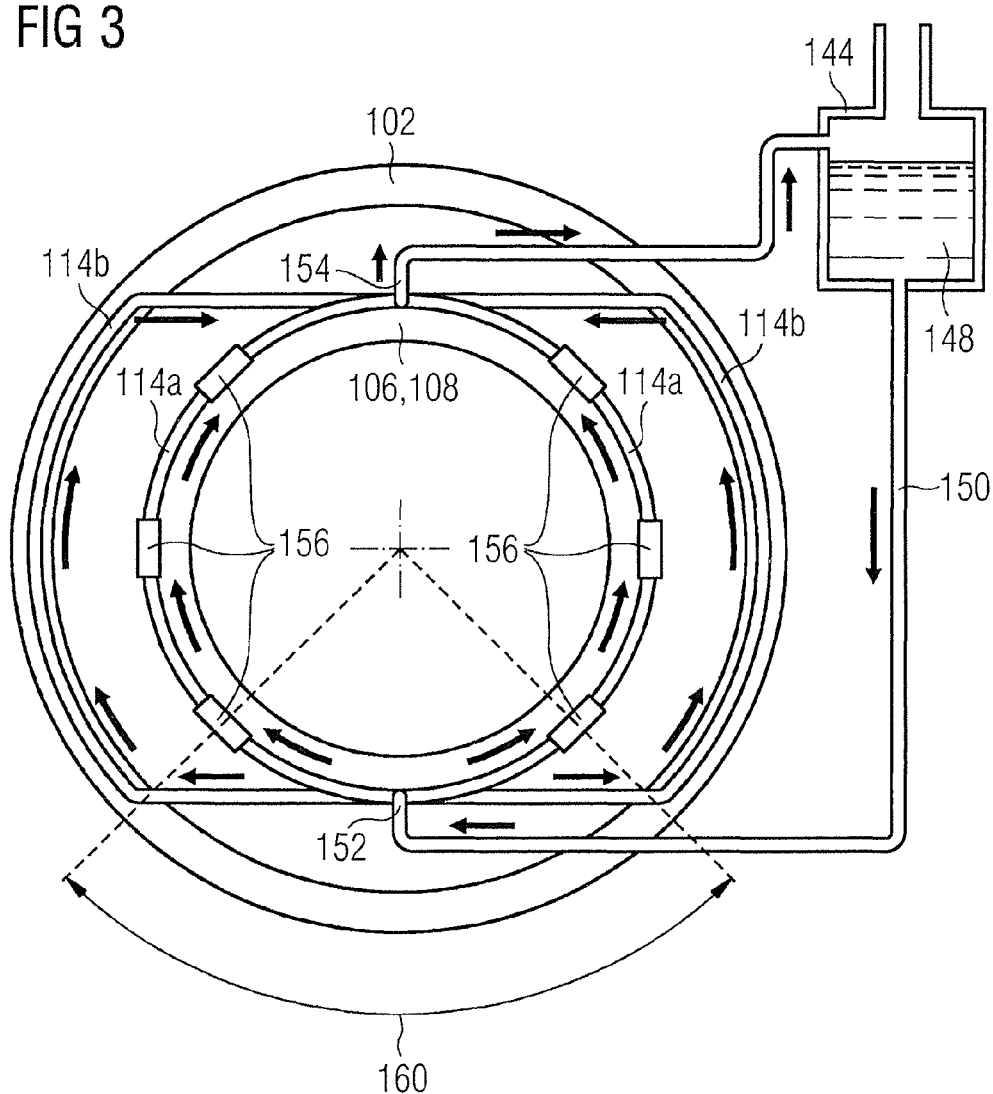
FIG. 3 shows an axial view of a coil arrangement with cooling, similar to that shown in FIG. 2, and suitable for inclusion in a combined MRI and radiation therapy system of the preferred embodiments invention.

FIG. 3 shows an axial end-view of the structure of FIG. 2. Features corresponding to features shown in FIG. 1 or FIG. 2 carry corresponding reference numerals. The arrangement of feed and return pipes in the remote reservoir 144 differs from that in FIG. 2, and shows an alternative arrangement. Either arrangement may be used, or any other which ensures a higher pressure of cryogen at the opening of the feed tube 150 as compared to the pressure at the opening of the return tube. A certain lower section 160 of the shield coils 102, and a corresponding certain upper section of the shield coils are cooled by conduction cooling through a thermally conductive cooling strap or thermally conductive member extending around each shield coil. This simplifies the tubing required and enables a gravity fed return even from the uppermost point of the shield coil cooling circuit.

In alternative embodiments, the radiation source 202 and gimbal arrangement 203 may be positioned within the OVC, in the central region 180, in which case it is not necessary to provide gamma-transparent portions 131 of the OVC.

In some embodiments, the field coils 102 may not be required. In some embodiments, the gimbal arrangement may not include the facility to tilt the radiation source 202, such that the radiation source is constrained to rotate about the axis of the essentially cylindrical the field coil structure 104 in the central region 180, so as to direct a beam of radiation essentially radially through the essentially cylindrical field coil structure 104.

The present exemplary embodiments therefore provide a combined MRI and radiation therapy system comprising a non-split superconducting magnet with a 'gamma-transparent' central region. This is achieved by using gamma-transparent materials, typically using materials of low atomic number, preferably carbon or graphite composites, in the OVC, thermal shield and magnet support structure.

Cooling of the coils of the superconducting magnet is provided by the use of a cooling loop arrangement, where the upper and lower collector manifolds are linked by radiation transparent elements at the mid-plane.

The optional realization of a 'waisted' cryostat design enables the accommodation of a gantry carrying a radiation source and collimator mounted such as to occupy much the same space envelope as a conventional cylindrical MRI magnet.

Although preferred exemplary embodiments are shown and described in detail in the drawings and in the preceding specification, they should be viewed as purely exemplary and not as limiting the invention. It is noted that only preferred exemplary embodiments are shown and described, and all variations and modifications that presently or in the future lie within the protective scope of the invention should be protected.

I claim as my invention:

1. A combined MRI and radiation therapy system, comprising:

a magnet structure and radiation therapy equipment;

the magnet structure comprising a single cylindrical field coil structure comprising a number of superconducting coils joined by a support structure that extends continuously through a central region of said cylindrical field coil structure in which no superconducting coils are present, a single outer vacuum chamber enclosing all of the field coil structure in one evacuated volume, said outer vacuum chamber comprising an outer vacuum chamber wall having a continuous wall portion that is co-extensive with said central region, and a cooling arrangement comprising cooling tubes that are separate from said support structure and that are in thermal contact with the superconducting coils and out of thermal contact with said support structure, and arranged to receive a cryogen flowing through the cooling tubes, at least some of said cooling tubes proceeding through said central region; and the radiation therapy equipment comprising a gamma radiation source mounted in the central region for rotation about an axis of the cylindrical field coil structure that proceeds through in the central region so as to direct a radiation beam along a selected path radially through the central region, and said support structure and the wall portion of the outer vacuum chamber and any portion of said cooling tubes that proceed through the central region within any path of the radiation beam being comprised of material that is transparent to radiation emitted by the gamma radiation source, so the radiation beam passes through the field coil structure and the outer vacuum chamber and said portion of said cooling tubes without substantial interference from the field coil structure and the outer vacuum chamber and said portion of the cooling tubes.

2. The combined MRI and radiation therapy system according to claim 1 wherein the gamma radiation source is mounted to tilt so as to selectively direct the radiation beam along a selected path at a selected non-zero angle with respect to said axis.

3. The combined MRI and radiation therapy system according to claim 1 comprising a gimbal arrangement in which the gamma radiation source is mounted.

4. The combined MRI and radiation therapy system according to claim 3 wherein an axially central portion of the outer vacuum chamber in said central region has a lesser outer diameter than an outer diameter of portions of the outer vacuum chamber on said opposite sides of said central region thereby defining a toroidal cavity, and wherein the gimbal arrangement and the gamma source are accommodated within the toroidal cavity.

5. The combined MRI and radiation therapy system according to claim 4 comprising an outer cover that covers said toroidal cavity.

6. The combined MRI and radiation therapy system according to claim 1 comprising a thermal radiation shield between the field coil structure and the outer vacuum chamber, the thermal radiation shield having a shield region in the central region that is transparent to the radiation emitted by the gamma radiation source, so the radiation beam is directed through the thermal radiation shield without substantial interference from the thermal radiation shield.

7. The combined MRI and radiation therapy system according to claim 1 wherein the magnet structure comprises shield coils having a diameter that is larger than the field coil structure in said central region.

8. The combined MRI and radiation therapy system according to claim 1 wherein a part of said support structure that extends through said central region, and said wall portion, are comprised of material selected from the group consisting of beryllium, carbon, and aluminum.

9. The combined MRI and radiation therapy system according to claim 1 wherein a part of said support structure that extends through said central region, and said wall portion, are comprised of resin-impregnated carbon fiber.

10. The combined MRI and radiation therapy system according to claim 1 wherein the cooling arrangement comprises upper and lower manifolds of said cooling tubes that extend through the central region with only parts of the cooling tubes in the manifolds in the central region within any path of the radiation beam being transparent to the radiation emitted by the gamma radiation source, so the radiation beam is directed through the manifolds without substantial interference from the manifolds.

11. The combined MRI and radiation therapy system according to claim 10 wherein a part of said support structure that extends through said central region, and said wall portion, are comprised of a ceramic.

* * * * *